United States Patent
Dobson et al.

(10) Patent No.: US 6,466,807 B1
(45) Date of Patent: Oct. 15, 2002

(54) OPTICAL GLUCOSE DETECTOR

(75) Inventors: Peter J. Dobson, Oxford; Scott J. Turner, Bicester, both of (GB)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/485,472

(22) PCT Filed: Aug. 5, 1998

(86) PCT No.: PCT/GB98/02352

§ 371 (c)(1),
(2), (4) Date: Jul. 17, 2000

(87) PCT Pub. No.: WO99/07278

PCT Pub. Date: Feb. 18, 1999

(30) Foreign Application Priority Data

Aug. 12, 1997 (GB) .............................. 9717134

(51) Int. Cl.⁷ ................................................ A61B 5/00
(52) U.S. Cl. ...................... 600/316; 600/322; 600/310
(58) Field of Search ................. 600/309–310, 600/322–326, 316, 476, 473; 356/39–41

(56) References Cited

U.S. PATENT DOCUMENTS

| | | | | |
|---|---|---|---|---|
| 4,281,645 A | * | 8/1981 | Jobsis | 600/324 |
| 5,370,114 A | * | 12/1994 | Wong et al. | 600/322 |
| 5,379,764 A | | 1/1995 | Barnes et al. | |
| 5,529,755 A | | 6/1996 | Higashio et al. | |
| 5,553,613 A | | 9/1996 | Parker | |
| 5,601,080 A | * | 2/1997 | Oppenheimer | 600/322 |
| 5,743,262 A | * | 4/1998 | Lepper, Jr. et al. | 600/316 |
| 5,782,756 A | * | 7/1998 | Mannheimer | 600/322 |
| 5,818,048 A | * | 10/1998 | Sodickson | 250/343 |
| 5,830,132 A | * | 11/1998 | Robinson | 600/310 |

FOREIGN PATENT DOCUMENTS

| | | |
|---|---|---|
| EP | 0 623 308 | 11/1994 |
| WO | 90/07905 | 7/1990 |
| WO | 92/00513 | 1/1992 |
| WO | 93/17621 | 9/1993 |
| WO | 94/04070 | 3/1994 |
| WO | 95/22046 | 8/1995 |
| WO | 96/14567 | 5/1996 |
| WO | 96/41151 | 12/1996 |

* cited by examiner

*Primary Examiner*—Eric F. Winakur
*Assistant Examiner*—Matthew Kremer
(74) *Attorney, Agent, or Firm*—David L. Weinstein

(57) ABSTRACT

A device for the in vivo measurement of the concentration of an analyte in an aqueous solution comprises a transmitter for illuminating a body part with light at a plurality of predetermined wavelengths. A detector receives light from such body part and generates input signals representative of the intensity of received light at each of the predetermined wavelengths, and a computer coupled to the detector generates an output signal representative of the analyte concentration in the body part by analysis of the input signals received from the detector. The detector is adapted to generate input signals representative of the intensity of light received at three discrete wavelengths, and a formula is provided for calculating the output signal on the basis thereof.

16 Claims, 3 Drawing Sheets

OPTICAL GLUCOSE DETECTOR

This invention relates to the optical detection of glucose in body fluids, particularly in blood. It is concerned especially with in vivo detection in which a detection device is applied to part of the body, or a part of the body to the device, and a signal generated indicating the glucose concentration level in a non-invasive manner.

There are two primary known optical techniques by which the concentration of glucose (or any other analyte) can be detected. One involves the direct measurement of the transmitted intensity of light at the various ligand vibrational wavelengths, and relating this to the molecular concentration by the Beer-Lambert law, for example, modified to allow for scattering. The other exploits the fact that solutes such as glucose modify the water vibration and combination of overtone lines in unique ways. This is because of water molecule clustering effects around the solute molecules. Because many water molecules are involved for each solute molecule, the effect is quite large and likely to offer better sensitivity than the direct measurement technique referred to above. Both techniques benefit from using a full spectrum; i.e, by monitoring transmissivity over a wide range of wavelengths, and spectral recognition and quantification algorithms can also be used. However, while apparatus using these techniques can give accurate results, it is likely to be expensive, primarily because of the cost of suitable optical detectors.

As with the second technique described above, the present invention exploits the effect that glucose and other analytes have on the water vibration and combination overtone lines in predominantly aqueous solutions such as blood. At certain predeterminable wavelengths, the optical characteristics of such a solution exhibit readily quantifiable changes from which can be derived an indication of the concentration of the analyte in the solution. For example, when glucose is added to water, the vibration overtone/combination features of the water are reduced in magnitude in the absorption spectrum. This is because the glucose molecules replace some of the water; i.e. the relative molecule occupied by the water is reduced. There are also other changes to the shape of the water overtones due to the ice-like structure of water molecules around the solute. The net result of these effects is that at least two specific wavelengths, there is a substantial variation in the transmissivity of the solution relative to a reference level at which for another identifiable wavelength the transmissivity is unaltered.

According to the invention, a device for the in vivo measurement of the concentration of an analyte in an aqueous solution comprises a transmitter for illuminating a body part with light at a plurality of predetermined wavelengths; a detector for receiving light from such body part and generating input signals representative of the intensity of received light at each of the predetermined wavelengths; and a computer coupled to the detector for generating an output signal representative of the analyte concentration in the body part by analysis of the input signals received from the detector.

The detector in preferred devices of the invention is adapted to generate input signals representative of the intensity of light received at three discrete wavelengths. A suitable formula for calculating the output signal ($S_o$) from light received at three discrete wavelengths is as follows:

$$S_o = \log \frac{I_B}{I_A} - \frac{I_C}{I_A}$$

where $I_A$ is representative of the intensity of received light a reference wavelength A, upon which the analyte has little effect;

$I_B$ is representative of the intensity of received light as a second wavelength B at which the presence of the analyte has the effect of increasing the transmissivity of the solution; and $I_C$ is representative of the intensity of received light at a third wavelength C upon which the presence of the analyte has the effect of reducing the transmissivity of the solution, and wherein C>B>A.

For glucose in water or blood, wavelength A is typically 810 nm; wavelength B is 970 nm; and wavelength C is 1053 nm. A particular advantage of wavelengths in this range is that relatively inexpensive detectors such as silicon diodes, can be used.

In the above description of the technique of the invention, reference has been made primarily to the transmissivity of the aqueous solution. Indeed, the operation of a device embodying the invention can best be understood by reference to direct transmission, and measurements can be made of sugar concentrations in blood for example, by monitoring the transmissivity of light through a body part such as a finger or an ear lobe. However, the technique is equally applicable when diffused light reflected from a part of the body is monitored rather than light which has been transmitted through a body part. In this respect it should be recognised that a diffuse reflectance spectrum from a scatterer such as body tissue is a quasi-absorption spectrum because of the multiplicity of the scattering.

Devices embodying the invention can use polychromatic (white) light as the source of illumination with appropriate filters disposed in front of the detectors for each selected wavelength. This is a very simple arrangement, but could be prone to errors in condition of high background light and is likely to suffer from a poor signal/noise ratio. A more preferred arrangement uses tuned laser diodes or light emitting diodes with appropriate filtering as respective light sources. The advantage is that the transmitted or reflected light can be detected using a single photodiode. Established analytical techniques can be used to derive a concentration signal using the formula set out above. Whatever the nature of the light source or sources used, we have found that stable output light intensity is important. Preferably the light intensity should be stabilized to one part in 10,000. Stabilization can be carried out over time periods of thirty minutes. Alternatively, means may be provided for monitoring the light output intensity and for effecting correction as required.

Devices embodying the invention can take a number of forms. "Transmission" devices can comprise a light clamping mechanism for fitting over an ear lobe or finger for example, and where applied to a body part with significant bone content, provision may be made for squeezing the body part to project a fleshy section into the path of the transmitted light. Another such device takes the form of an enclosure fitted with transmission and detection apertures, into which a respective body part is inserted. In all these cases, effective optical contact between a respective body part and the transmitter and detector respectively can be enhanced by the provision of an index matching fluid between them, which has the effect of minimising the influence of extraneous light, and collimating light within the optical circuit.

Devices embodying the invention and using the diffuse reflectance variation can be of relatively more simple construction in that the point from which light is transmitted to the body part and the point at which reflected light is received can be located adjacent one another on the same instrument, typically in the same plane. Smaller amounts of impedance matching fluid can be required, and these variations of the device have the added advantage of being suitable for application to many parts of the body with relatively little concern for the presence of bone. They can also be used inside the mouth, where the exposed tissue is particularly well suited for measurement of blood characteristics. Further, reflectance devices may be adapted to include a pressure monitor for gauging the compliance of the skin being contacted. This itself is an indication of the nature of the tissue under examination and the quantity of blood flowing therein. Of course, the greater the concentration of blood in the relevant tissue section, the more accurate can be the analysis of analyte concentrations in the blood.

Devices embodying the invention can be constructed for personal use by individuals needing to regularly monitor their blood sugar levels, such as diabetes sufferers. Discrete devices for hand use can be provided but in some variants, the device can be attached or worn at substantially all times to enable the user to continuously monitor the relevant concentrations. For example, the device could be strapped to the body in the same manner as is a wrist watch. A device may also be equipped with an alarm which activates in response to dangerous changes in a sugar level, and a monitoring device with this feature will be of particular value for use with a sleeping subject.

Further features of the invention will become apparent from the following description in which a number of embodiments will be described, and in which reference will be made to the accompanying schematic drawings wherein.

Figure 1:
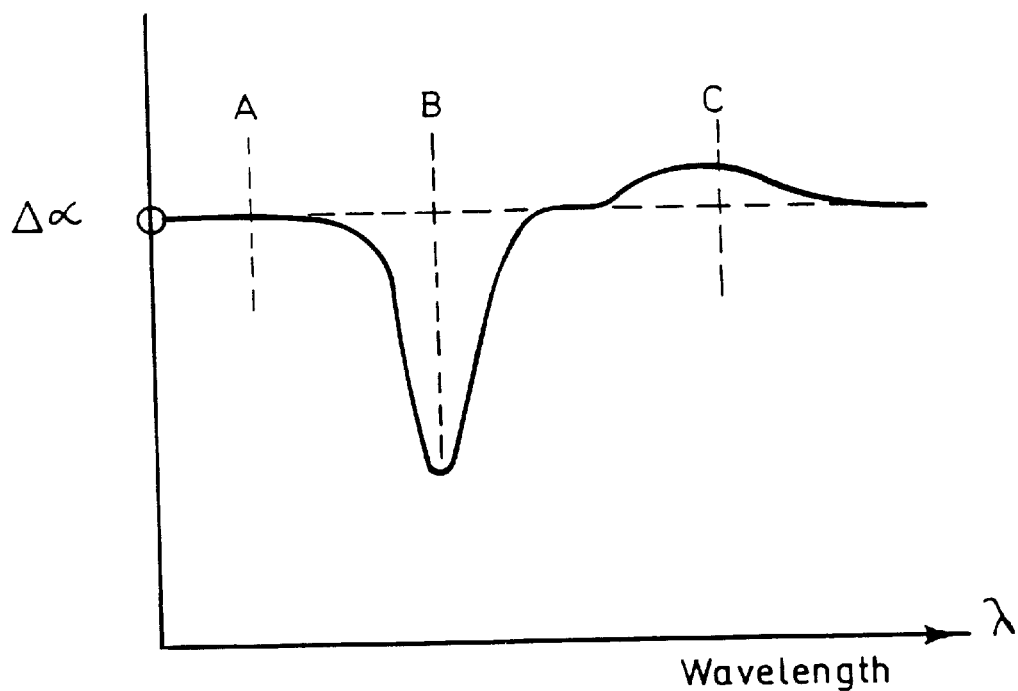
FIGS. 1 and 2 are graphs of light absorption and of transmissivity respectively plotted against wavelength for a solution of glucose in water.

When glucose is added to water, the vibration overtone/ combination features of the water are reduced is magnitude in the absorption spectrum. This is because the glucose molecules replace some of the water i.e. the relative volume occupied by water is reduced. There are also other changes to the shape of the water overtones due to the ice-like structuring of water molecules around the solute. The net result of these effects can be seen in the difference absorption spectra curve shown schematically in FIG. 1. At A, the spectrum of an aqueous solution does not change. At B, there is a marked reduction in absorption due to the excluded volume and structure modification by the solute and at C there is an increase in absorption due to the solute. For glucose in water, B is at 970 nm (an overtone/combination wavelength of water) and C is at 1053 nm (an overtone/ combination wavelength of $CH_2$).

Figure 2:
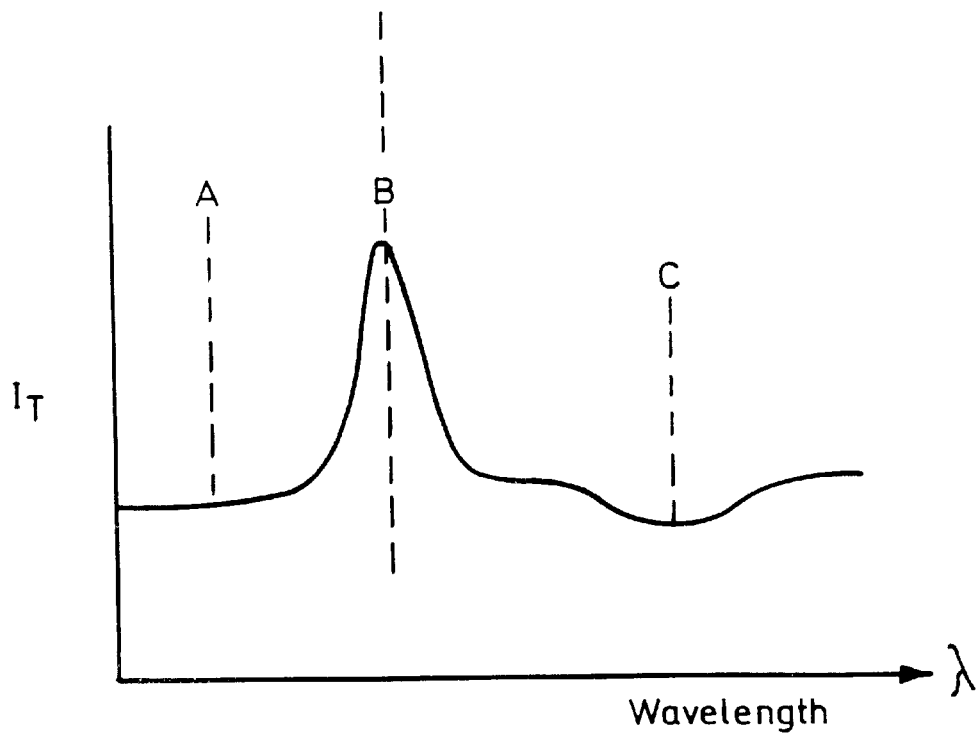

By measuring the transmitted intensities at wavelengths A, B and C it is possible to quantify the amount of glucose present in the water. The wavelength A is best selected to be the isobestic wavelength for oxygenated and de-oxygenated haemoglobin (810 nm) and this is used as a reference to allow for the complex light scattering in tissue. The transmitted light intensities will now appear as in FIG. 2 and the glucose concentration $S_o$ will be proportional to $$\log \frac{I_B - I_A}{I_A} - \frac{I_C - I_A}{I_A}$$

This quantity can easily be measured for an individual and calibration factors can be estimated.

Figure 3:
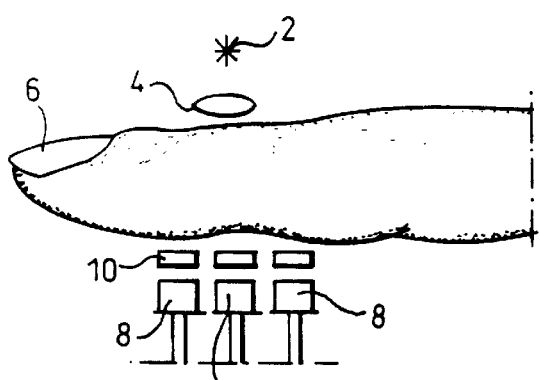
FIGS. 3 and 4 illustrate two embodiments of the invention in which transmitted light is analysed.
Figure 4:
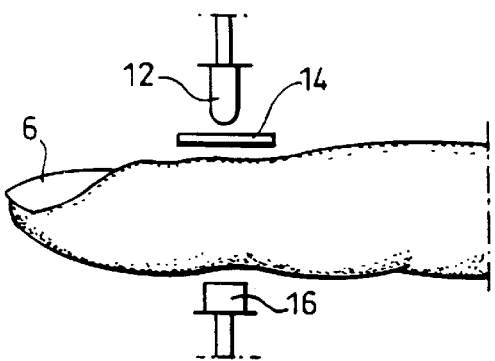

In the embodiments of FIGS. 3 and 4, light is transmitted through a human finger, and monitored by detectors in the form of photodiodes. In FIG. 3 the transmitter is a source of white light, directed through a lens 4 towards the section of a finger just below the nail 6. Three photodiodes 8 are disposed at an opposite face of the finger, each protected by a filter 10, to receive light at respective predetermined wavelengths from the source. In FIG. 4, three laser diodes or light emitting diodes (LED) 12 with filters 14 are disposed around the surface of the finger just below the nail 6 to transmit light at the three predetermined wavelengths as in the embodiment of FIG. 3. Laser diodes would be tuned to the respective wavelengths; the filters 14 would only be required with LEDs. Transmitted light is received by a single photodiode 16, which can separately monitor light at the various different wavelengths.

Figure 5:
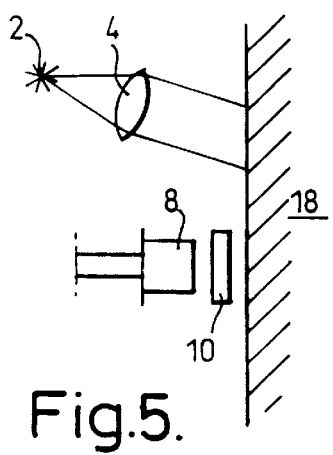
FIGS. 5 and 6 illustrate two embodiments of the invention in which diffused reflected light is analysed.
Figure 6:
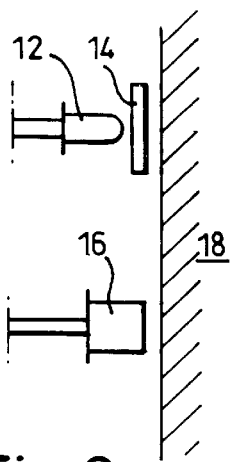

The embodiments of FIGS. 5 and 6 function in broadly the same manner as those of FIGS. 3 and 4 respectively, and the same reference numerals are used. However, in these examples the monitored light is diffused light reflected through the same surface of a body part at which the transmitted light is directed, thereby reducing the effect of intervening components such as bone in the finger illustrated in FIGS. 3 and 4.

Figure 7:
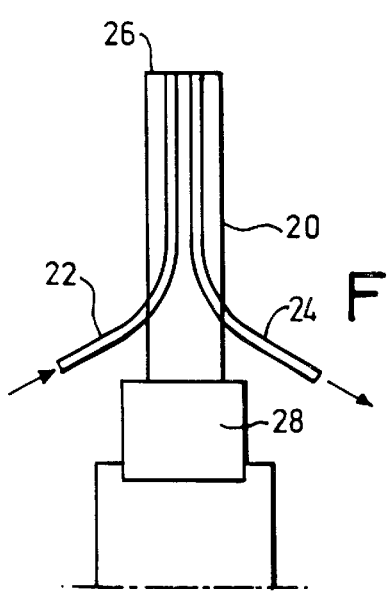
FIG. 7 illustrates an embodiment of the invention which analyses diffused reflective light, and for ready application to a wide variety of body parts.

FIG. 7 illustrates a device embodying the principals of FIGS. 5 and 6. The device comprises a probe 20 in which fibre optic cables 22 and 24 are mounted for transmitting light to an engagement surface 26, and transmitting reflected light therefrom. The surface 26 is designed to engage or otherwise optically contact the surface of a body part (not shown) in which light transmitted along optical fibre 22 is diffused and reflected along optic fibre 24. The Figure shows the optical fibres actually leaving the probe, and it is certainly quite possible that the light source and detector and computer equipment can be disposed in a separate assembly. In some circumstances, and certainly when the invention is embodied in a diagnostic instrument for institutional use, the instrument itself would house the relevant additional equipment.

Also shown in the embodiment of FIG. 7 is a force transducer mechanism 28 which can be used to measure the compliance of the tissue section under examination. By applying pressure at the remote end of the probe, the transducer can monitor the relative displacement of the end, and thereby the resistance offered by the examined tissue. This provides further data for consideration by the computer in its analysis of the various input signals it receives.

FIG. 8 is divided into three sections A, B and C as in practice the analysis of the input signals received by the computer from the detector will comprise three discrete and identifiable stages.

Figure 8A:
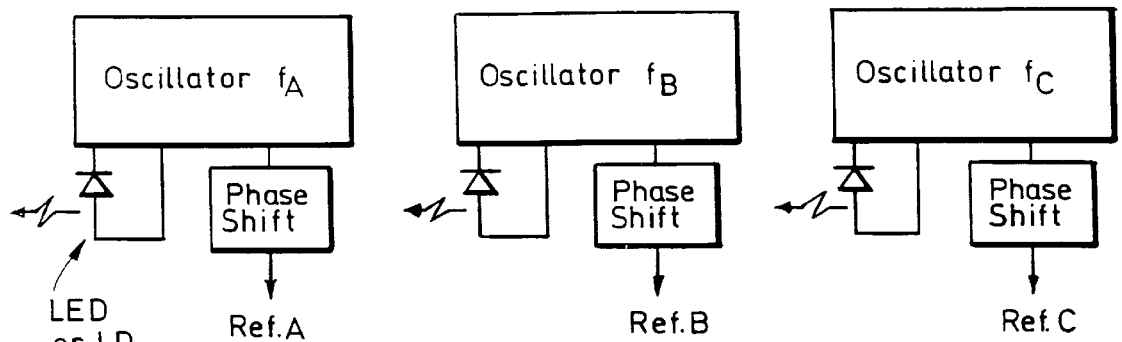
FIGS. 8A, 8B, and 8C illustrate sections of a suitable analysing circuit for generating the analyte concentration signal from the input light signals.
Figure 8B:
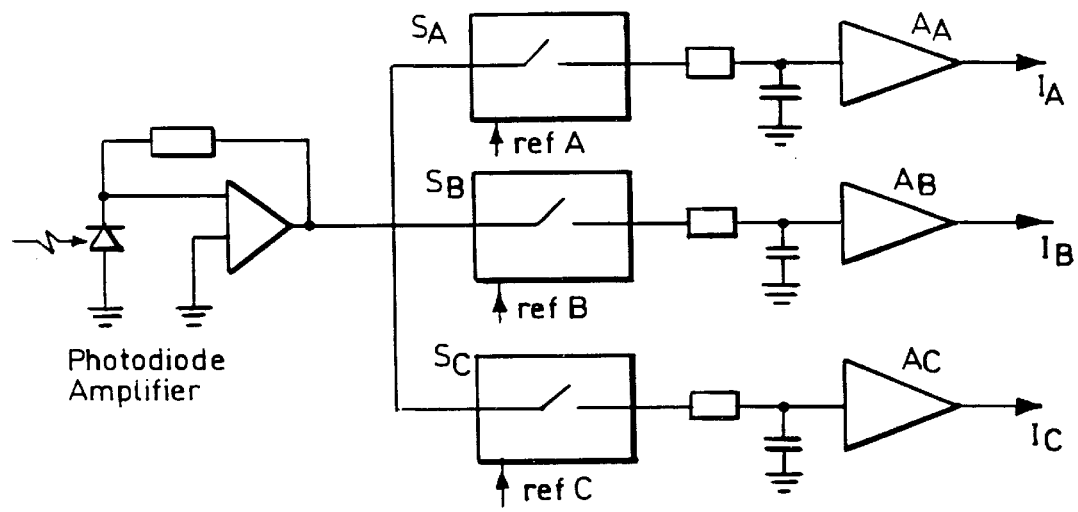
Figure 8C:
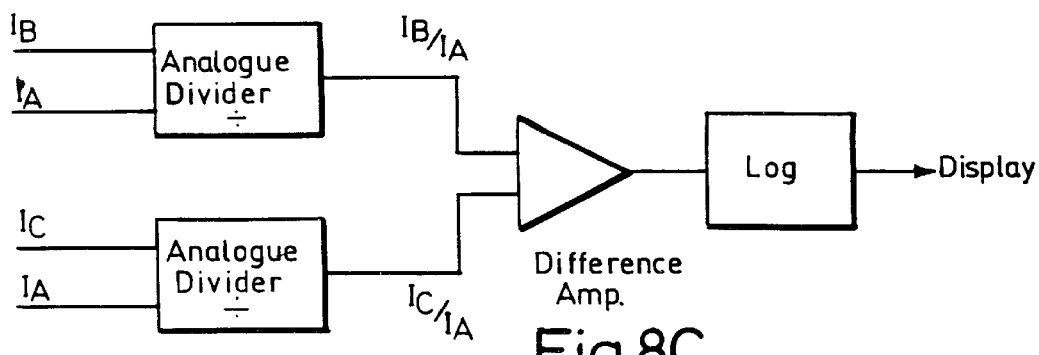

FIG. 8A shows the LED or LD driver circuitry, each diode being modulated at a different frequency (typically a few hundred or thousand Hz). The light signals are detected by a single photodiode (FIG. 8B) and the photocurrent is converted into a voltage by A, and this signal is de-coded by the CMOS switches $S_A$, $S_B$, $S_C$ each of which is driven from the modulation reference signals A, B, C. The signals are amplified after the low pass filters by amplifiers $A_A$, $A_B$ and $A_C$ to give outputs which are proportional to $I_A$, $I_B$ and $I_C$. These outputs are then divided and subtracted by the circuit of FIG. 8C. The output can be further processed and used to drive a meter (LCD or analogue). This particular implementation will have a very good tolerance to ambient light, and offer excellent signal/noise performance.

The output may be used to drive a simple meter or display which can be calibrated for the individual. Another feature of this idea is that a "calibration check" sample could be provided; this could take the form of an artificial "finger" or a pad. The display could be extremely simple, in the form of an LCD bar display to tell the user if his/her glucose level is going up or down.

While the invention has been described herein primarily with reference to the measurement of sugar concentrations in aqueous solutions, particularly glucose in blood, it will be appreciated that the technique described is applicable to the analysis of other analyte levels and in other liquids. Different discrete wavelengths will be applicable for different analyte/ solution combinations, and these can be determined by constructing graphs of the kind illustrated in FIGS. 1 and 2 for such solutions. The specific wavelengths for the variations at B and C will be the same for the given solution, notwithstanding the different concentrations of analyte therein. Further, while the calculation of the analyte concentration level has been described on the basis of intensity measurements of transmitted light at three discrete wavelengths, it should be recognised that for most solutions there are identifiable variations in the absorption spectra also at a number of other wavelengths. The intensity of transmitted light at these other wavelengths can also be used as the basis for analyte concentration level calculations.

What is claimed is:

1. A device for measuring concentration of an analyte in blood comprising a transmitter for illuminating a body part with light at a plurality of predetermined wavelengths; a detector for receiving light from said body part and generating input signals representative of the intensity of the received light at each said wavelength; and a computer coupled to the detector for generating an output signal representative of the concentration of the analyte in the blood in said body part by analysis of input signals received from the detector, wherein the output signal $S_o$ is generated from the following formula:

$$S_o = \log\frac{I_B}{I_A} - \frac{I_C}{I_A}$$

where $I_A$ is representative of the intensity of received light at wavelength A at which the transmissivity of the blood is unaltered by the analyte;

$I_B$ is representative of the intensity of received light at wavelength B at which the transmissivity of the blood is increased by the analyte;

$I_C$ is representative of the intensity of received light at wavelength C at which the transmissivity of the blood is reduced by the analyte; and

C>B>A.

2. A device according to claim 1 wherein the detector is adapted to generate input signals representative of the intensity of light received at three discrete wavelengths.

3. A device according to claim 1 wherein the analyte is glucose, and wherein A is 810 nm B is 970 nm and C is 1053 nm.

4. A device according to claim 1 wherein the transmitter and detector are mounted in a housing for disposition on either side of body part such that the detector receives light from the transmitter after passage through the body part.

5. A device according to claim 1 wherein the transmitter and detector are mounted in a housing for disposition against adjacent sections of tissue on body part such that the detector receives light from the transmitter after diffuse reflection within the body part.

6. A device according to claim 5 including a force transducer for gauging compliance of tissue against which the body part is disposed.

7. A device according to claim 1 wherein the transmitter comprises a source of white light, and the detector comprises photo-diodes for separately monitoring receipt of light at the predetermined wavelengths.

8. A device according to claim 1 wherein the transmitter comprises a plurality of light sources respectively for generating light at the predetermined wavelengths; and a photo-diode for monitoring the receipt of such light.

9. A device according to claim 1 wherein light from the transmitter is delivered along at least one optical fibre.

10. A device according to claim 1 wherein light is delivered to the detector along at least one optical fibre.

11. A device according to claim 1 wherein light from the transmitter is delivered along at least one optical fibre and light is delivered to the detector along at least one optical fibre, further including a contact section having a surface for engaging a body part, the optical fibres from and to the transmitter and detector terminating at said surface.

12. A method of measuring concentration of an analyte in blood comprising a illuminating a body part with light at a plurality of predetermined wavelengths; monitoring light at said wavelengths received from the body part and generating input signals representative of the intensity thereof; and generating an output signal representation of the concentration of the analyte in the blood in said body part by analysis of input signals, wherein the output signal $S_o$ is generated from the following formula:

$$S_o = \log\frac{I_B}{I_A} - \frac{I_C}{I_A}$$

where $I_A$ is representative of the intensity of received light at wavelength A at which the transmissivity of the blood is unaltered by the analyte;

$I_B$ is representative of the intensity of received light at wavelength B at which the transmissivity of the blood is increased by the analyte;

$I_C$ is representative of the intensity of received light at wavelength C at which the transmissivity of the blood is reduced by the analyte; and

C>B>A.

13. A method according to claim 12 wherein the detector generates input signals representative of light received at three discrete wavelengths.

14. A method according to claim 12 wherein the analyte is glucose, and wherein A is 810 nm B is 970 nm C is 1053 nm.

15. A method according to claim 12 wherein the light received by the detector has passed through said body part.

16. A method according to claim 12 wherein the light received by the detector is generated by diffuse reflection in said body part.

* * * * *

UNITED STATES PATENT AND TRADEMARK OFFICE
CERTIFICATE OF CORRECTION

PATENT NO. : 6,466,807 B1  
DATED : October 15, 2002  
INVENTOR(S) : Peter J. Dobson et al.

It is certified that error appears in the above-identified patent and that said Letters Patent is hereby corrected as shown below:

Title page,
Item 57, ABSTRACT, replace the word "comprises" with the word -- comprising --.

Column 5,
Line 39, replace the word "said" with the word -- such --.

Signed and Sealed this

Sixth Day of May, 2003

JAMES E. ROGAN
*Director of the United States Patent and Trademark Office*